United States Patent [19]

Allen, Jr. et al.

[11] 4,117,130

[45] Sep. 26, 1978

[54] METHOD FOR TREATING ANXIETY IN MAMMALS

[75] Inventors: George Rodger Allen, Jr., Old Tappan, N.J.; John William Hanifin, Jr.; Daniel Bryan Moran, both of Suffern, N.Y.; Jay Donald Albright, Nanuet, N.Y.

[73] Assignee: American Cyanamid Company, Stamford, Conn.

[21] Appl. No.: 853,724

[22] Filed: Nov. 21, 1977

Related U.S. Application Data

[63] Continuation of Ser. No. 735,475, Oct. 26, 1976, abandoned.

[51] Int. Cl.² ........................................... A61K 31/495
[52] U.S. Cl. .................................................. 424/250
[58] Field of Search .................. 424/250; 260/250 AC

[56] References Cited

FOREIGN PATENT DOCUMENTS 1,187,281 4/1970 United Kingdom ............. 260/250 AC

OTHER PUBLICATIONS

Deev et al., Chem. Abst., 82-125338 R, (1973).
Yurugi et al., Chem. Abst., 80-37073 D, (1973).

*Primary Examiner*—Stanley J. Friedman
*Attorney, Agent, or Firm*—Edward A. Conroy, Jr.

[57] ABSTRACT

This disclosure describes compositions of matter useful as anxiolytic agents and the method of meliorating anxiety in mammals therewith; the active ingredients of said compositions of matter being certain substituted 6-phenyl-1,2,4-triazolo[4,3-b]pyridazines or the pharmacologically acceptable acid-addition salts thereof.

10 Claims, No Drawings

METHOD FOR TREATING ANXIETY IN MAMMALS

CROSS REFERENCE TO RELATED APPLICATION

This application is a continuation of our copending application Ser. No. 735,475, filed Oct. 26, 1976, now abandoned.

BRIEF SUMMARY OF THE INVENTION

This invention relates to novel compositions of matter useful as anxiolytic agents. More particularly, it relates to therapeutic compositions containing certain substituted 6-phenyl-1,2,4-triazolo[4,3-b]pyridazines or the non-toxic acid-addition salts thereof which meliorate anxiety in mammals. The invention includes the new compositions of matter and the method of meliorating anxiety in mammals therewith. The substituted 6-phenyl-1,2,4-triazolo[4,3-b]pyridazines of the present invention may be represented by the following structural formula:

wherein $R_1$, $R_2$, and $R_3$ are each individually selected from the group consisting of hydrogen and alkyl having up to 3 carbon atoms; and $R_4$ is meta or para chloro, bromo, fluoro, cyano, trifluoromethyl, nitro or amino with the proviso that at least one of $R_1$ and $R_2$ is hydrogen.

DETAILED DESCRIPTION OF THE INVENTION

The active compounds of the present invention are generally obtainable as white to pale yellow crystalline materials having characteristic melting points and absorption spectra and which may be purified by recrystallization from common organic solvents such as methanol, ethanol, dimethylformamide, acetone, chloroform, ethyl acetate, and the like. They are appreciably soluble in non-polar organic solvents such as toluene, carbon tetrachloride, and the like but are relatively insoluble in water. These organic bases form non-toxic acid-addition salts with a variety of pharmacologically acceptable organic and inorganic salt-forming reagents. Thus, acid-addition salts, formed by admixture of the organic free base with one or two equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. The acid-addition salts are relatively insoluble in non-polar organic solvents such as diethyl ether, benzene, toluene, and the like but are appreciably soluble in water. For purposes of this invention, the free bases are equivalent to their non-toxic acid-addition salts.

The active compounds of the present invention may be readily prepared in accordance with the following reaction scheme:

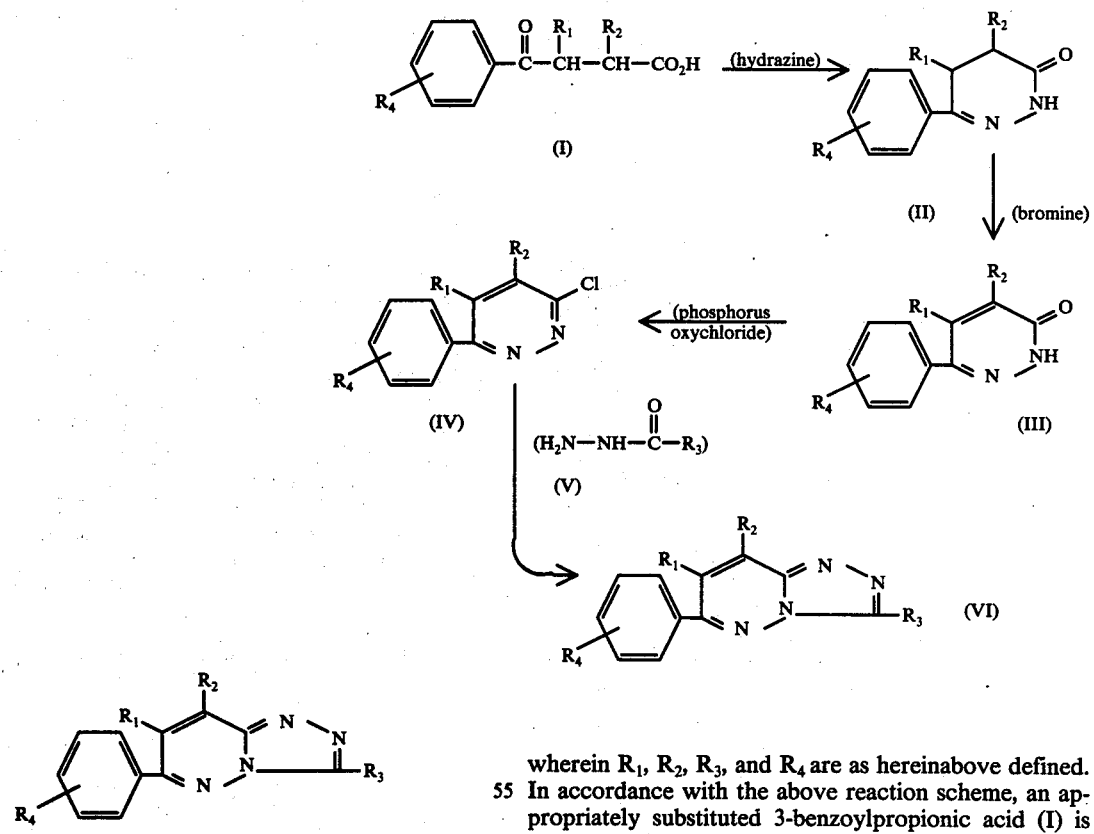

wherein $R_1$, $R_2$, $R_3$, and $R_4$ are as hereinabove defined. In accordance with the above reaction scheme, an appropriately substituted 3-benzoylpropionic acid (I) is reacted with hydrazine hydrate at the reflux temperature in a lower alkanol solvent for a period of 12-24 hours to provide the corresponding 4,5-dihydro-6-phenyl-3(2H)-pyridazinone (II). Treatment of the 4,5-dihydro-6-phenyl-3(2H)-pyridazinone (II) with bromine in glacial acetic acid solvent at steam bath temperature for a period of 2-4 hours provides the corresponding 6-phenyl-3(2H)-pyridazinone (III). Conversion of the 6-phenyl-3(2H)-pyridazinone (III) to the corresponding 3-chloro-6-phenylpyridazine (IV) is achieved by treatment with excess phosphorus oxychloride at steam bath temperature for a period of 4-8 hours. Interaction of the 3-chloro-6-phenylpyridazine (IV) with an acylhydrazine (V) at the reflux temperature in a lower alkanol solvent for a period of 24–48 hours provides the corresponding 6-phenyl-1,2,4-triazolo[4,3-b]pyridazines (VI) of the present invention.

The active compounds of the present invention may also be readily prepared in accordance with the following reaction scheme:

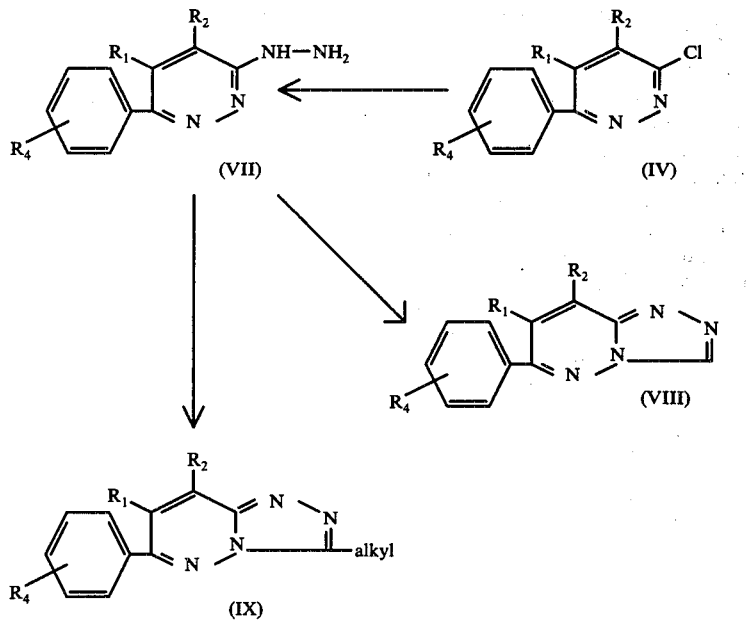

wherein $R_1$, $R_2$, and $R_4$ are as hereinabove defined. In accordance with the above reaction scheme, an appropriately substituted 3-chloro-6-phenylpyridazine (IV) is reacted with hydrazine hydrate at the reflux temperature in a lower alkanol solvent for a period 12–24 hours to provide the corresponding 3-hydrazino-6-phenylpyridazine (VII). Ring closure of the 3-hydrazino derivatives (VII) with lower alkyl orthoformates provides compounds of formula (VIII) wherein $R_3$ is hydrogen. Ring closure of the 3-hydrazino derivatives (VII) with lower alkanoic acid anhydrides, lower alkanoic acid chlorides, or orthoesters of lower alkanoic acids provides compounds of formula (IX) wherein $R_3$ is lower alkyl. The ring closures may be carried out with or without catalysis by bases such as pyridine or tri(lower alkyl) amines. Ring closures with lower alkyl orthoformates and orthoesters of lower alkanoic acids are preferably carried out without catalysis and without solvent, although an inert solvent may be used. The ring closures are usually accomplished by heating with or without a solvent at 50° C. to 175° C.

The active compounds of the present invention possess central nervous system activity at non-toxic doses and as such are useful as anxiolytic agents. That is, they produce certain responses in standard tests with laboratory animals which are known to correlate well with relief of anxiety in man. The compounds have been tested pharmacologically and found to have such properties with a desirable wide spread between doses producing anxiolytic activity and toxic symptoms. The anti-anxiety properties of the active compounds of the present invention have been established in a test which indicates anxiolytic activity by the measure of protection from convulsions resulting from the administration of pentylenetetrazole. Graded dose levels of the test compounds were administered orally, in a 2% starch vehicle, to groups of at least 5 rats. At the estimated time of peak effect, the rats were treated intravenously with pentylenetetrazole at a dose of 21 to 23 mg./kg. of body weight. This dose is estimated to cause clonic seizures in 99% of unprotected rats. The effective dose ($ED_{50}$) of the test compound for protection of 50% of the animals is calculated by the method of D. H. Finney in "Statistical Methods in Biological Assay", Second Edition, Hafner Publishing Co., New York, 1964, pp. 456–457. Representative results are given in Table I which follows in comparison with chlordiazepoxide and meprobamate, which were tested in exactly the same manner. It has been reported [R. T. Hill and D. H. Tedeschi, "Animal Testing and Screening Procedures in Evaluating Psychotropic Drugs" in "An introduction to Psychopharmacology", Eds, R. R. Rech and K. E. Moore, Raven Press, New York, pp. 237–288 (1971)] that there is a high degree of correlation between antagonism of pentylenetetrazole seizures in rats and anti-anxiety effects in higher warm-blooded animals.

TABLE I

Protection Against Clonic Seizures Caused By Pentylenetetrazole In Rats

| Compound | | | | Median Effective |
|---|---|---|---|---|
| $R_1$ | $R_2$ | $R_3$ | $R_4$ | Oral Dose (mg./kg.) |
| H | H | H | 3-chloro | 8.2 |
| H | H | $CH_3$ | 3-trifluoromethyl | 1.7 |
| H | H | $CH_3$ | 4-fluoro | 3.4 |
| H | H | H | 3-amino | 15 |
| $CH_3$ | H | H | 3-cyano | 34 |
| H | H | H | 4-fluoro | 5 |
| H | H | H | 4-chloro | 9.8 |
| H | H | H | 3-trifluoromethyl | 2.5 |

TABLE I-continued
Protection Against Clonic Seizures Caused By Pentylenetetrazole In Rats

| Compound | | | | Median Effective |
|---|---|---|---|---|
| R$_1$ | R$_2$ | R$_3$ | R$_4$ | Oral Dose (mg./kg.) |
| Chlordiazepoxide | | | | 2.5 |
| Meprobamate | | | | 22 |

The active compounds of the present invention have thus been found to be highly useful for meliorating anxiety in mammals when administered in amounts ranging from about 0.03 milligram to about 10.0 mg. per kilogram of body weight per day. A preferred dosage regimen for optimum results would be from about 0.1 mg. to about 5.0 mg. per kilogram of body weight per day, and such dosage units are employed that a total of from about 7.0 milligram to about 0.35 gram of active compound for a subject of about 70 kg. of body weight are administered in a 24 hour period. The dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compounds may be administered in any convenient manner such as by the oral, intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 0.1 and 5.0 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The invention will be described in greater detail in conjunction with the following specific examples.

EXAMPLE 1

Preparation of p-(7-methyl-1,2,4-triazolo[4,3-b]pyridazin-6-yl)benzonitrile

A 200 g. portion of p-(1,4,5,6-tetrahydro-4-methyl-6-oxo-3-pyridazinyl)benzonitrile [Journal of Medicinal Chemistry 17, 281(1974)] is suspended in 500 ml. of glacial acetic acid with overhead stirring at steam bath temperature, then 56 ml. of liquid bromine is dissolved in an additional 500 ml. of acetic acid and this solution is added to the stirring mixture all at once. After approximately half an hour of heating, a vigorous exothermic reaction occurs with the expulsion of the excess bromine and hydrogen bromide. The reaction mixture is then diluted with 4 liters of distilled water and the resulting solid is filtered and the filter cake is copiously washed with water and is air dried. This material is recrystallized from a large amount of ethyl alcohol to afford the product p-(1,6-dihydro-4-methyl-6-oxo-3-pyridazinyl)benzonitrile as a white solid.

A 45.9 g. portion of the above material and 250 ml. of phosphorus oxychloride is heated at steam bath temperature for 3 hours. The excess phosphorus oxychloride is decomposed by the slow addition of the reaction mixture to crushed ice with stirring. The resulting solid is filtered, washed with water and dried in vacuo. The material is then recrystallized from methyl alcohol to give p-(6-chloro-4-methyl-3-pyridazinyl)benzonitrile.

A mixture of 14.6 g. of the above compound, 9.4 g. of formylhydrazine and 175 ml. of butyl alcohol is stirred at reflux for 18 hours. The reaction mixture is concentrated free of solvent and the concentrate is triturated with petroleum ether and is filtered. The filter cake is air dried and the yellow solid is recrystallized twice from methyl alcohol, the resulting light yellow crystals are again recrystallized from methanol to afford the product of the example, m.p. 240°–243° C.

EXAMPLE 2

Preparation of p-(3,7-dimethyl-1,2,4-triazolo[4,3-b]pyridazin-6-yl)-benzonitrile A 1.48 g. portion of acetic acid hydrazide is dissolved in 50 ml. of butyl alcohol with heating, then 4.58 g. of p-(6-chloro-4-methyl-3-pyridazinyl)benzonitrile (prepared as in Example 1) is added and complete solution occurs after heating for an additional 10 minutes. The solution is then heated at reflux for 18 hours. The reaction mixture is concentrated to afford 5.8 g. of orange solid which is washed with petroleum ether. This product is dissolved in 1:1 ethyl alcohol/acetone and is filtered through a pad of silica gel. The filter is washed copiously with acetone and the combined filtrates are concentrated to a yellow solid. The solid is dissolved in 100 ml. of acetone and the solution is cooled in dry ice-acetone to afford a tan solid which is collected by filtration, washed copiously with petroleum ether and air dried. This product is dissolved in methyl alcohol, is treated with activated charcoal and is filtered. The filtrate is used to recrystallize 1.06 g. of yellowish crystals. A 500 mg. portion of the above is recrystallized twice from methanol and the resultant product is dried in vacuo to give the product of the example, m.p. 242°–244° C.

EXAMPLE 3

Preparation of p-(3-ethyl-7-methyl-1,2,4-triazolo[4,3-b]pyridazin-6-yl)benzonitrile A mixture of 102.13 g. of ethyl propionate, 50 g. of hydrazine hydrate and 150 ml. of ethyl alcohol is stirred at reflux for 24 hours. The reaction mixture is concentrated free of solvent, then is cooled in ice and stirred with petroleum ether. A white solid results which is filtered, washed with petroleum ether and is dried in vacuo to afford propionic acid hydrazide as a white crystalline solid.

A 30.8 g. portion of the above compound is dissolved in one liter of butyl alcohol (dried over 3-A molecular sieves), then 40.0 g. of p-(6-chloro-4-methyl-3-pyridazinyl)-benzonitrile (prepared as in Example 1) is added and the reaction mixture is allowed to heat at reflux for 18 hours. The reaction mixture is concentrated free of solvent and the concentrate is triturated with petroleum ether, then is filtered. The filter cake is vacuum dried to afford a yellow solid which is then recrystallized from methyl alcohol to give the product of the example, m.p. 192°–195° C.

EXAMPLE 4

Preparation of 7-methyl-6-(m-nitrophenyl)-1,2,4-triazolo[4,3-b]pyridazine

A 28 g. portion of 3-(m-nitrobenzoyl)butyronitrile [prepared as described in J. Org. Chem., Vol. 38, No. 23, 4044–4048 (1973)] is added to one liter of 6N hydrochloric acid and is stirred at reflux for one hour using a magnetic stirrer and a heating mantle. The reaction mixture is cooled and extracted with methylene chloride. The organic layer is separated and extracted with saturated sodium bicarbonate. The bicarbonate layer is added dropwise to a stirred cold hydrochloric acid solution and the resulting solid is kept cold in ice then is filtered and air dried to afford 27.24 g. of 3-m-nitrobenzoyl butyric acid as a white solid. The entire amount of the preceding compound is mixed with 12.8 ml. of 99% hydrazine hydrate in 140 ml. of ethyl alcohol and is stirred at reflux for 3 hours. A solid begins to appear after about half an hour. The reaction mixture is cooled in an ice bath and the resulting solid is filtered and air dried to afford the compound 4,5-dihydro-5-methyl-6-(m-nitrophenyl)-3(2H)-pyridazinone as white to light yellow crystals.

A 24.9 g. portion of the above material is dissolved in 200 ml. of warm stirred glacial acetic acid, then 6.2 ml. of bromine dissolved in 50 ml. of glacial acetic acid is added to this dropwise over a 15 minute period with the evolution of hydrogen bromide gas. The reaction mixture is warmed for an additional 20 minutes to expel the hydrogen bromide, then the mixture is poured into crushed ice. The resulting solid is filtered and washed with large amounts of water then is dried in vacuo to afford 24.2 g. of 5-methyl-6-(m-nitrophenyl)-3(2H)-pyridazinone as a cream colored solid.

A 22.7 g. portion of the preceding compound is combined with 230 ml. of phosphorus oxychloride and heated on a steam bath for 3 hours. The reaction mixture is poured portionwise into crushed ice with stirring. The resulting solid is filtered, copiously washed with water and air dried to yield 15.6 g. of 3-chloro-5-methyl-6-(m-nitrophenyl)pyridazine as a tan solid.

A mixture of 14.97 g. of the compound above, 7.2 g. of formylhydrazine and 200 ml. of butyl alcohol is stirred at reflux for 18 hours. The reaction mixture is decanted free of insolubles and the liquid portion is cooled in an ice bath to afford 13.28 g. of brown crystalline solid. This material is dissolved in 300 ml. of boiling methyl alcohol then is filtered to remove insolubles. The filtrate is clarified by treatment with activated charcoal and filtering. This filtrate is concentrated to a small volume and cooled to yield a tan-brown solid as the product of the example, m.p. 213°–218° C.

EXAMPLE 5

Preparation of 6-(m-aminophenyl)-7-methyl-1,2,4-triazolo[4,3-b]pyridazine

A mixture comprising 2.28 g. of 7-methyl-6-(m-nitrophenyl)-1,2,4-triazolo[4,3-b]pyridazine (prepared as described in Example 4), 100 ml. of ethyl alcohol and a catalytic amount of platinum oxide is shaken in a Parr shaker under 40 pounds of hydrogen pressure for 1½ hours. The reaction mixture is filtered free of catalyst and the filtrate is concentrated to afford the product of the example as a yellow solid, m.p. 182°–186° C.

EXAMPLE 6

Preparation of 6-(p-bromophenyl)-1,2,4-triazolo[4,3-b]pyridazine

A mixture of 3.76 g. of 3-(p-bromophenyl)-6-chloropyridazine, 1.80 g. of formylhydrazine and 50 ml. of butyl alcohol is heated to reflux and allowed to reflux overnight. The reaction mixture is allowed to cool and the precipitated product is washed with water, air dried and recrystallized from methyl alcohol, m.p. 209°–211° C.

EXAMPLE 7

Preparation of 6-(p-fluorophenyl)-1,2,4-triazolo[4,3-b]pyridazine

An 87 g. sample of 6-(p-fluorophenyl)-4,5-dihydro-3(2H)-pyridazinone (prepared as in U.S. Pat. No. 3,689,652, Example 5) is stirred in 800 ml. of glacial acetic acid in a 2 liter 3 necked flask on a steam bath. A solution of 24.1 ml. of bromine liquid in 100 ml. of glacial acetic acid is prepared in a dropping funnel. A 15 ml. portion of this bromine solution is added dropwise to the reaction mixture which is heated with stirring until the mixture becomes lighter in color. The remainder of the bromine solution is then added with heating and stirring over about 30 minutes. The reaction mixture is then heated for one hour longer then is poured onto crushed ice. The solid formed is collected by filtration, washed with water and air dried overnight. The material is then dried at 65° C. to afford 82.0 g. of 6-(p-fluorophenyl)-3(2H)-pyridazinone as crystals, m.p. 265°–268° C.

The entire amount of the above compound is combined with 500 ml. of phosphorus oxychloride and is heated on a steam bath for 5 hours. The reaction mixture is cooled and the excess phosphorus oxychloride is removed using a rotary evaporator, then one liter of ice-water is added with stirring. The resulting solid is filtered, washed with water and air dried overnight. The solid is taken up in 2 liters of chloroform, treated with activated charcoal and filtered through diatomaceous earth. The chloroform filtrate is concentrated to a low volume, the precipitate formed is collected by filtration and washed with chloroform, then air dried to afford 3-chloro-6-(p-fluorophenyl)pyridazine as pinkish crystals.

A 2.5 g. portion of the above compound is mixed with 1.46 g. of formylhydrazine and 40 ml. of butyl alcohol. The mixture is heated to reflux and is refluxed overnight. The mixture is cooled in an ice bath and the precipitated product is collected by filtration, is washed with butyl alcohol and is dried overnight. The dried material is recrystallized from methyl alcohol to give the product of the example as crystals, m.p. 197°–198° C.

EXAMPLE 8

Preparation of p-(1,2,4-triazolo[4,3-b]pyridazin-6-yl)benzonitrile

An 86.3 g. sample of 6-(p-bromophenyl)-4,5-dihydro-3(2H)-pyridazinone (prepared as in U.S. Pat. No. 3,689,652, Example 4) is dissolved in 500 ml. of glacial acetic acid by heating to 80° C. with continuous stirring. A solution of 60 g. of bromine in 80 ml. of acetic acid is added dropwise at 75°–80° C. over a one hour period. A solid is separated near the end of the addition. The reaction mixture is heated with stirring on the steam bath for half an hour more, then is poured into 3 liters of cracked ice-water. The white solid formed is collected by filtration and is air dried. The product is then recrystallized from ethyl alcohol to afford 6-(p-bromophenyl)-3(2H)-pyridazinone.

A mixture of 19.20 g. of the product above and 9.10 g. of cuprous cyanide in 70 ml. of dimethylformamide is stirred at reflux temperature for 5½ hours. A solid is precipitated during this time. The hot mixture is poured into a solution of 46 ml. of ethylenediamine in 230 ml. of water. The mixture is stirred at ice-bath temperature for 30 minutes, the precipitate is collected by filtration and washed with water until the washings are colorless to afford p-(1,6-dihydro-6-oxo-3-pyridazinyl)benzonitrile as a yellow solid.

A stirred solution of 3.42 g. of the preceding material in 25 ml. of phosphorus oxychloride is heated at reflux temperature for 3 hours. Most of the excess phosphorus oxychloride is removed under reduced pressure then cracked ice-water is added to the concentrate which is stirred. The solid is collected by filtration and after air-drying is recrystallized from dimethylformamide-water to give p-(6-chloro-3-pyridazinyl)benzonitrile as crystals, m.p. 236°–238° C.

A mixture of 1.00 g. of the above product, 0.84 g. of formylhydrazine and 25 ml. of n-butyl alcohol is stirred at reflux temperature for 17 hours and 45 minutes. The solvent is removed under reduced pressure and the residue is triturated with ethyl alcohol. The mixture is filtered and the solid is recrystallized from dimethylformamide-water to afford p-(1,2,4-triazolo[4,3-b]pyridazin-6-yl)benzonitrile as an orange solid, m.p. 272°–274° C.

EXAMPLE 9

Preparation of m-(7-methyl-1,2,4-triazolo[4,3-b]pyridazin-6-yl)benzonitrile

A 15 g. portion of m-(1,4,5,6-tetrahydro-4-methyl-6-oxo-3-pyridazinyl)benzonitrile [Journal of Medicinal Chemistry 17, 281 (1974)] is suspended in 75 ml. of glacial acetic acid with stirring at steam bath temperature. Then 3.75 ml. of bromine in 25 ml. of acetic acid is added dropwise over a 15 minute period. The reaction mixture is heated on a steam bath for an additional 30 minutes then is poured onto crushed ice. The resulting solid is collected by filtration, copiously washed with water and dried to afford m-(1,6-dihydro-4-methyl-6-oxo-3-pyridazinyl)benzonitrile as a cream colored solid.

A 10.0 g. portion of the above material and 100 ml. of phosphorus oxychloride is heated on a steam bath for 3 hours. The excess phosphorus oxychloride is decomposed by the slow addition of the reaction mixture to cold water with stirring. The resulting solid is filtered and the filter cake is copiously washed with water. The product is air dried to afford m-(6-chloro-4-methyl-3-pyridazinyl)benzonitrile as a cream colored solid.

A mixture of 3.0 g. of the above compound, 1.57 g. of formylhydrazine and 100 ml. of butyl alcohol is stirred at reflux for 18 hours. The reaction mixture is cooled in an ice bath and filtered to collect the solid formed. The product of the example is then recrystallized from methyl alcohol to afford a cream colored solid, m.p. 214°–216° C.

EXAMPLE 10

Preparation of
3-propyl-6-(α,α,α-trifluoro-m-tolyl)-1,2,4-triazolo[4,3-b]pyridazine A 112 g. portion of p-toluenesulfonic acid is dissolved in 500 ml. of tetrahydrofuran with stirring. Then 106 g. of morpholine is added portionwise with stirring. A 95.63 g. portion of m-trifluoromethylbenzaldehyde is added and the reaction mixture is stirred at reflux for 2 hours. The reaction mixture is cooled and a solution of 42.2 g. of potassium cyanide in 75 ml. of water is added. The mixture is then allowed to stir at reflux overnight. The reaction mixture is concentrated free of solvent and the concentrate is partitioned between water and chloroform. The organic layer is washed with saturated sodium bisulfite, dried over magnesium sulfate, treated with activated charcoal and filtered. The filtrate is concentrated in vacuo to afford α-(α,α,α-trifluoro-m-tolyl)-4-morpholineacetonitrile as a dark yellow oil. A 67.0 g. portion of the oil above is dissolved in two liters of tetrahydrofuran with stirring at room temperature. Stirring is continued while eight 10 ml. portions of ethyl acrylate and nine 5 ml. portions of a 30% solution of potassium hydroxide in ethyl alcohol are added to the reaction mixture over a 5 hour period. This reaction is slightly exothermic. The reaction mixture is allowed to stir at room temperature overnight. The mixture is treated with activated charcoal and filtered. The filtrate is concentrated free of solvent then is stripped several times with toluene. The concentrate is stirred with diethyl ether and filtered to remove insolubles. The filtrate is concentrated to a yellow oil then is chromatographed on a 75 cm. × 8 cm. glass column containing silica gel with chloroform as the solvent. The chromatographed material is stripped of chloroform to afford 47.0 g. of γ-cyano-γ-(α,α,α-trifluoro-m-tolyl)-4-morpholinebutyric acid as a yellow oil. The entire amount of the preceding product is combined with two liters of ethyl alcohol and 7.3 ml. of hydrazine hydrate. The mixture is stirred at reflux for 18 hours, then is concentrated free of solvent to afford a yellow oil which is stirred with petroleum ether to yield 14.55 g. of 4,5-dihydro-6-(α,α,α-trifluoro-m-tolyl)-3(2H)-pyridazinone as a white solid. The total amount of the product above is dissolved in 225 ml. of glacial acetic acid at ambient temperature, then 3.33 ml. of bromine is dissolved in 25 ml. of acetic acid and 2.5 ml. of this solution is added to the starting material above at room temperature. The reaction mixture is warmed on a steam bath for half an hour while the remaining bromine-acetic acid solution is added dropwise. Following complete discoloration, the reaction mixture is heated on a steam bath for half an hour, and is concentrated free of solvent. The solid concentrate is washed with water, filtered and air dried to afford 6-(α,α,α-trifluoro-m-tolyl)-3(2H)-pyridazinone as a cream colored solid.

A 12.55 g. portion of the above product and 200 ml. of phosphorus oxychloride is heated on a steam bath for 18 hours. The reaction mixture is concentrated free of excess phosphorus oxychloride and the concentrate is triturated with cold water. The resulting solid is filtered and the filter cake is washed with water. The material is air dried to afford 3-chloro-6-(α,α,α-trifluoro-m-tolyl)-pyridazine as a cream colored solid.

A mixture of 6.0 g. of the preceding product, 4.74 g. of butyric acid hydrazide and 75 ml. of butyl alcohol is allowed to stir at reflux for 48 hours. The reaction mixture is concentrated free of solvent and the concentrate is taken up in ethyl alcohol, treated with activated charcoal and filtered. The filtrate is concentrated to a small residue, cooled in an ice bath and the resulting solid is filtered to afford the product of the example as a cream colored solid. This material is recrystallized from ethyl alcohol and dried in vacuo to afford crystals, m.p. 118°–120° C.

EXAMPLE 11

Preparation of
6-(p-bromophenyl)-7-methyl-1,2,4-triazolo[4,3-b]pyridazine

A 10.0 g. portion of 6-(p-bromophenyl)-5-methyl-3(2H)-pyridazinone [Journal of Medicinal Chemistry 17, 281 (1974)] and 100 ml. of phosphorus oxychloride is heated at steam bath temperature for 3 hours. The mixture is added dropwise to cold water while stirring. The resulting solid is filtered and washed with water to afford 3-(p-bromophenyl)-6-chloro-4-methylpyridazine as a grey solid.

A mixture of 1.5 g. of the above compound, 0.64 g. of formylhydrazine and 25 ml. of butyl alcohol is stirred at reflux for 18 hours. The reaction mixture is cooled in an ice bath, filtered and the solid is recrystallized from methyl alcohol to afford the product of the example as a yellow solid, m.p. 219°–222° C.

EXAMPLE 12

Preparation of
6-(p-chlorophenyl)-3-methyl-1,2,4-triazolo[4,3-b]pyridazine

A 47.5 g. portion of 6-(p-chlorophenyl)-4,5-dihydro-3(2H)-pyridazinone (prepared as in Example 1 of U.S. Pat. No. 3,689,652) is dissolved in 250 ml. of glacial acetic acid at 65°–70° C. with stirring. Then a solution of 14 ml. (42 g.) of bromine liquid in 50 ml. of acetic acid is added portionwise during a 20 minute period. The reaction mixture is stirred at 65° C. for 3 hours and is cooled to 4° C. The precipitate is collected and washed with 100 ml. of ethyl acetate. The solid is suspended in 500 ml. of water, 25 ml. of concentrated ammonium hydroxide is added and the mixture is stirred at room temperature overnight. The precipitate is collected, washed with 500 ml. of water and dried at 60° C. to afford 6-(p-chlorophenyl)-3(2H)-pyridazinone.

A mixture of 34.5 g. of the preceding material and 150 ml. of phosphorus oxychloride is refluxed for 4 hours. The reaction mixture is cooled and poured into 2 kg. of ice. After standing for 2 hours with occasional stirring, the precipitate is collected and washed with water. The solid is dissolved in 500 ml. of boiling benzene, clarified with activated charcoal and filtered. The filtrate is cooled to room temperature and the solid is collected, washed with a small amount of benzene and air dried. This material is recrystallized from ethyl alcohol after treatment with activated charcoal. The product is collected, washed with ethyl alcohol followed by ether to afford 3-chloro-6-(p-chlorophenyl)pyridazine, m.p. 209°–211° C.

A mixture of 10.0 g. of the product above, 6.6 g. of hydrazine hydrate and 150 ml. of butyl alcohol is refluxed overnight. The reaction mixture is cooled, filtered and the solid washed with butyl alcohol and with water. The butyl alcohol filtrate above is concentrated on a rotating evaporator and additional crystalline product is obtained which is washed with butyl alcohol and with water. The combined material affords 6-(p-chlorophenyl)-3-hydrazinopyridazine, m.p. 156°–160° C.

A mixture of 6.6 g. of the above material (prepared in the manner described), 140 ml. of p-dioxane and 4.64 g. of diisopropylethylamine is warmed until solution occurs. The solution is then cooled to near room temperature and 2.66 g. of acetyl chloride is added. The reaction mixture is then cooled in an ice bath and allowed to stir overnight. The solvent is then removed under vacuum and ethyl alcohol is added to the residue. The flask is warmed and the solid is precipitated. This material is removed by filtration and the ethanol is further concentrated to afford the product of the example as crystals, m.p. 208°–210° C.

EXAMPLE 13

Preparation of 6-(p-chlorophenyl)-8-methyl-1,2,4-triazolo[4,3-b]pyridazine

To a solution of 114 g. of methylsuccinic anhydride in 400 ml. of chlorobenzene is added carefully 270 g. of aluminum chloride. The mixture is heated to 65° C. for 1½ hours, is cooled, quenched with ice and concentrated hydrochloric acid and extracted with benzene. The benzene layer is extracted with aqueous sodium bicarbonate. After adjusting the pH of the bicarbonate solution to 6.3, concentrated hydrochloric acid is added slowly over a period of several hours with stirring. At pH 5.7, 78 g. of white crystals are filtered off. Recrystallization of this material from ethanol-water affords 3-(p-chlorobenzoyl)-2-methylpropionic acid as white crystals. A mixture of 35.50 g. of the preceding compound, 85 ml. of hydrazine hydrate and 400 ml. of ethyl alcohol is allowed to stir at reflux for 18 hours. The reaction mixture is concentrated to about 75% of the original volume, cooled in an ice bath and filtered to yield 26.62 g. of 6-(p-chlorophenyl)-4,5-dihydro-4-methyl-3(2H)-pyridazinone as a yellow solid. An additional 4.7 g. of product is obtained from the filtrate above.

The combined product above (31.32 g.) is dissolved in 250 ml. of glacial acetic acid at room temperature with stirring. An 8.2 ml. portion of liquid bromine is dissolved in 50 ml. of glacial acetic acid and 25% of this solution is added to the reaction mixture. The temperature of the reaction mixture is increased until all the coloration due to bromine is gone. The remaining bromine solution is added with warming over a 20 minute period. The reaction mixture is warmed on the steam bath for an additional one-half hour and is diluted with ice water. The resulting solid is filtered, washed with water and air dried to afford 6-(p-chlorophenyl)-4-methyl-3(2H)-pyridazinone as a cream colored solid.

A 15.0 g. portion of the preceding compound and 200 ml. of phosphorus oxychloride is heated on a steam bath for 18 hours. The reaction mixture is concentrated free of solvent and the concentrate is stirred with cold water. The precipitate is filtered and the solid is warmed with water to afford 3-chloro-6-(p-chlorophenyl)-4-methylpyridazine as a pink solid.

A 2.0 g. portion of the compound above is mixed with 1.08 g. of formylhydrazine and 60 ml. of butyl alcohol. The mixture is refluxed for 48 hours. The reaction mixture is cooled in an ice bath and the resulting solid is filtered, washed with petroleum ether and air dried to afford a tan solid. The product of the example is recrystallized from methyl alcohol after treatment with activated charcoal to afford white crystals, m.p. 230°–233° C.

EXAMPLE 14

Preparation of 3-methyl-6-(α,α,α-trifluoro-m-tolyl)-1,2,4-triazolo[4,3-b]pyridazine A 6.0 g. portion of 3-chloro-6-(α,α,α-trifluoro-m-tolyl)pyridazine (prepared as in Example 10), 3.44 g. of acetylhydrazine and 75 ml. of n-butyl alcohol is refluxed for 48 hours. The solvent is removed under vacuum and the residue dissolved in ethyl alcohol and treated with activated carbon. The filtrate is concentrated, chilled and filtered to give an orange solid. Recrystallization from methyl alcohol affords the product of the example as crystals, m.p. 193°–194° C.

EXAMPLE 15

Preparation of 6-(p-chlorophenyl)-1,2,4-triazolo[4,3-b]pyridazine

A mixture of 9.0 g. of 3-chloro-6-(p-chlorophenyl)-pyridazine (prepared as in Example 12), 5.1 g. of formylhydrazine and 60 ml. of butyl alcohol is heated at reflux temperature for 40 hours. The reaction mixture is cooled, filtered and the solid washed with petroleum ether and with water. The material is then heated with 125 ml. of ethanol and the insoluble material is collected by filtration. The filtrate is cooled and the precipitate is collected and combined with the insoluble material collected above. The combined solids are recrystallized from 130 ml. of ethyl alcohol to provide the product of the example as crystals, m.p. 216°–218° C.

EXAMPLE 16

Preparation of 6-(α,α,α-trifluoro-m-tolyl)-1,2,4-triazolo[4,3-b]pyridazine

A mixture of 6.0 g. of 3-chloro-6-(α,α,α-trifluoro-m-tolyl)pyridazine (prepared as in Example 10), 2.78 g. of formylhydrazine and 75 ml. of butyl alcohol is allowed to stir at reflux temperature for 48 hours. The reaction mixture is concentrated free of solvent and the residue is dissolved in ethyl alcohol, treated with activated charcoal and filtered. The filtrate is cooled in an ice bath and the cream colored solid is collected. The solid is heated with diethyl ether and the mixture is filtered. The solid is recrystallized from ethyl acetate to afford the product of the example as cream colored crystals, m.p. 140°–143° C.

EXAMPLE 17

Preparation of 6-(p-chlorophenyl)-3-ethyl-1,2,4-triazolo[4,3-b]pyridazine

A mixture of 9.0 g. of 3-chloro-6-(p-chlorophenyl)-pyridazine (prepared as in Example 12), 7.4 g. of propionic acid hydrazide and 60 ml. of butyl alcohol is stirred at reflux temperature for 48 hours. The mixture is chilled, filtered and the solid is washed with petroleum ether and with water. The material is recrystallized from 50 ml. of ethyl alcohol to afford the product of the example as crystals, m.p. 197°–199° C.

EXAMPLE 18

Preparation of
6-(p-fluorophenyl)-3-methyl-1,2,4-triazolo[4,3-b]pyridazine

A mixture of 6.25 g. of 3-chloro-6-(p-fluorophenyl)-pyridazine (prepared as in Example 7), 4.65 g. of acetylhydrazine and 50 ml. of butyl alcohol is refluxed until a clear solution results. The reaction mixture is cooled, filtered, and the solid precipitate washed with hexane and with water. The solid is recrystallized from 50 ml. of ethyl alcohol to give the product of the example as crystals, m.p. 227°–229° C.

EXAMPLE 19

Preparation of
3-methyl-6-(m-nitrophenyl)-1,2,4-triazolo[4,3-b]pyridazine

A mixture of 9.9 g. of 6-(m-nitrophenyl)-4,5-dihydro-3-pyridazone [J. Med. Chem. 17, 273 (1974)] and 80 ml. of glacial acetic acid is stirred and heated on the steam bath and a solution of 2.41 ml. of bromine in 10 ml. of glacial acetic acid is added dropwise over a period of 30 minutes. Heating and stirring is continued for 45 minutes longer and the reaction mixture is poured onto crushed ice. The crystalline product is filtered and washed with water. The yield of 6-(m-nitrophenyl)-3-pyridazone, m.p. 275° C., is nearly quantitative.

A mixture of 6 g. of the above product and 35 ml. of phosphorus oxychloride is heated on a steam bath for 4 hours and concentrated to remove the excess $POCl_3$. The residue is poured into ice water and the insoluble solid is filtered, washed with water and air dried. The product is dissolved in chloroform, treated with activated carbon and clarified. The chloroform solution is concentrated to obtain 4.0 g. of 3-chloro-6-(m-nitrophenyl)pyridazine, m.p. 206°–208° C.

A mixture of 3.0 g. of the preceding compound, 2.0 g. of acetylhydrazine and 30 ml. of butanol is heated at reflux temperature for 72 hours and cooled. The precipitate is filtered, washed with hexane, with water, and air dried. The product is boiled with 100 ml. of 95% ethyl alcohol and filtered. The insoluble material, m.p. 241°–243° C., is 3-methyl-6-(m-nitrophenyl)-1,2,4-triazolo[4,3-b]pyridazine.

EXAMPLE 20

Preparation of
6-(m-nitrophenyl)-1,2,4-triazolo[4,3-b]pyridazine

The above compound, m.p. 231°–233° C., is obtained when formylhydrazine is substituted for acetylhydrazine in the procedure of Example 19.

EXAMPLE 21

Preparation of
6-(m-aminophenyl)-3-methyl-1,2,4-triazolo[4,3-b]pyridazine

A mixture of 5.1 g. of 3-methyl-6-(m-nitrophenyl)-1,2,4-triazolo[4,3-b]pyridazine (prepared as in Example 19), 60 ml. of trifluoroacetic acid and 0.9 g. of 10% palladium catalyst on carbon is shaken in a Parr hydrogenator under about 35 pounds of hydrogen pressure until hydrogen uptake is complete. The catalyst is filtered off and the reaction mixture is concentrated. The residue is dissolved in water and adjusted to pH 5 by addition of 5N NaOH. The insoluble material is filtered off and washed with water to obtain 6-(m-aminophenyl)-3-methyl-1,2,4-triazolo[4,3-b]pyridazine, m.p. 193° C.

EXAMPLE 22

Preparation of
6-(m-aminophenyl)-1,2,4-triazolo[4,3-b]pyridazine

The compound of the example, m.p. 225° C., is obtained when 6-(m-nitrophenyl)-1,2,4-triazolo[4,3-b]pyridazine (prepared as in Example 20) is reduced by the procedure of Example 21.

EXAMPLE 23

Preparation of
3-methyl-6-(p-tert-butylphenyl)-1,2,4-triazolo[4,3-b]pyridazine

A mixture of 16.5 g. of 3-p-tert-butylbenzoyl propionic acid [Journal Organic Chem. Soc. 19, 802 (1954)] and 8.25 ml. of hydrazine hydrate is dissolved in 140 ml. of absolute ethyl alcohol. The clear solution is stirred under reflux for 4 hours and chilled overnight. The product is collected, washed with ethyl alcohol and dried in vacuo to yield 13.1 g. of 6-(p-tert-butylphenyl)-4,5-dihydro-3(2H)-pyridazinone as a white solid.

An 8.00 g. portion of the preceding material in 80 ml. of glacial acetic acid is stirred while the dropwise addition of a solution of 5.82 g. of bromine in 20 ml. of glacial acetic acid is begun. The reaction mixture is heated to about 100° C. and decolorization occurs. The bromine/acetic acid solution is added as rapidly as decolorization occurs and is completed in about 15 minutes. The mixture is stirred for one hour at 100° C., then is poured into 150 ml. of ice. The white solid formed is collected by filtration, then is dissolved in 400 ml. of acetone. The acetone solution is dried over magnesium sulfate and is concentrated while diluting with hexane. Crystallization from about 100 ml. of acetone/hexane affords 4.82 g. of 6-(p-tert-butylphenyl)-3(2H)-pyridazinone as a light yellow solid.

A mixture of 22.8 g. of the above compound (prepared in the manner described) and 115 ml. of phosphorus oxychloride is warmed on a steam bath until a clear solution results. This solution is heated for 5 hours, then is concentrated in vacuo. The residue is treated with ice water and the resulting solid is collected and dried in vacuo to yield 22.0 g. of 3-(p-tert-butylphenyl)-6-chloropyridazine as an off-white solid.

A mixture of 5.0 g. of 3-(p-tert-butylphenyl)-6-chloropyridazine, 3.13 g. of acetylhydrazide and 50 ml. of n-butanol is refluxed for 48 hours. The mixture is concentrated under vacuum and the residue stirred with 100 ml. of water and 100 ml. of ether. The mixture is filtered to give 3.0 g. of tan solid, m.p. 144°–146° C. Recrystallization from acetone/hexane gives the product as pale yellow crystals, m.p. 142°–145° C.

EXAMPLE 24

Preparation of
6-(p-tert-butylphenyl)-1,2,4-triazolo[4,3-b[pyridazine

A mixture of 5.0 g. of 3-(p-tert-butylphenyl)-6-chloropyridazine, 2.54 g. of formylhydrazide and 50 ml. of n-butyl alcohol is stirred under reflux for 48 hours. The mixture is chilled and filtered. The solid is washed with petroleum ether and water and dried in vacuo to yield 0.80 g. of product. The filtrate is concentrated in vacuo below 80° C. to afford additional product which is stirred with 150 ml. of water and 150 ml. of diethyl ether, collected by filtration and dried in vacuo to yield 3.0 g. of an orange solid. Recrystallization from ethyl alcohol gives the product of the example as off-white crystals, m.p. 270°–275° C.

EXAMPLE 25

| Preparation of 50 mg. Tablets | | |
|---|---|---|
| Per Tablet | | Per 10,000 Tablets |
| 0.050 gm. | 3-methyl-6-(m-chloro-phenyl)-1,2,4-tria-zolo[4,3-b]pyridazine | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm | | 1490 gm. |

The 3-methyl-6-(m-chlorophenyl)-1,2,4-triazolo[4,3-b]pyridazine, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 26

| Preparation of Oral Suspension | |
|---|---|
| Ingredient | Amount |
| 3-ethyl-6-(m-fluorophenyl)-1,2,4-triazolo[4,3-b]pyridazine | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water qs to | 100 ml. |

The sorbitol solution is added to 40 ml. of distilled water and the 3-ethyl-6-(m-fluorophenyl)-1,2,4-triazolo[4,3-b]pyridazine is suspended therein. The saccharin, sodium benzoate, flavor and dye are added and dissolved. The volume is adjusted to 100 ml. with distilled water. Each ml. of syrup contains 5 mg. 3-ethyl-6-(m-fluorophenyl)-1,2,4-triazolo[4,3-b]pyridazine.

EXAMPLE 27

Preparation of Parenteral Solution

In a solution of 700 ml. of propylene glycol and 200 ml. of water for injection is suspended 20.0 grams of 3,7-dimethyl-6-(p-aminophenyl)-1,2,4-triazolo[4,3-b]pyridazine monohydrochloride with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 28

Preparation of 6-(p-chlorophenyl)-3,8-dimethyl-1,2,4-triazolo[4,3-b]pyridazine

A mixture of 1.0 g. of 3-chloro-6-(p-chlorophenyl)-4-methylpyridazine, 0.62 g. of acetic acid hydrazide and 10 ml. of n-butanol is refluxed for 48 hours. The solvent is removed and the residue dissolved in dichloromethane and filtered through magnesol. The solid from the filtrate is recrystallized from dichloromethane-hexane to give 0.6 g. of solid, m.p. 209°–212° C. Recrystallization from dichloromethane-hexane gives the product of the example as light pink colored crystals, m.p. 215°–217° C.

EXAMPLE 29

Preparation of 6-($\alpha,\alpha,\alpha$-trifluoro-p-tolyl)-1,2,4-triazolo[4,3-b]pyridazine A solution of 76.0 g. of p-toluenesulfonic acid in 400 ml. of tetrahydrofuran is cooled in an ice bath while 69.5 g. of morpholine is added. The cooling bath is removed and upon reaching ambient temperature 65.0 g. p-trifluoromethyl benzaldehyde is added followed by heating at reflux temperature for 2 hours. The reaction mixture is cooled in ice bath and a solution of 32.6 g. of potassium cyanide in 55 ml. of water added followed by heating at reflux temperature for 18 hours. The solvent is removed and the residue is partitioned between chloroform and water. The organic layer is washed with water, saturated sodium bisulfite and saturated sodium chloride solution, dried and evaporated to yield $\alpha$-($\alpha,\alpha,\alpha$-trifluoro-p-tolyl)-4-morpholineacetonitrile as a tan solid, m.p. 89°–90° C.

A solution of 52.3 g. of $\alpha$-($\alpha,\alpha,\alpha$-trifluoro-p-tolyl)-4-morpholineacetonitrile in 500 ml. of dry tetrahydrofuran is stirred at ambient temperature while 1 ml. portions of 30% potassium hydroxide in ethanol and 25 ml. portions of ethyl acrylate is added every half hour until a total of 5 ml. of the base and 150 ml. of ethyl acrylate is added. After the addition, the mixture is stirred at ambient temperature for 48 hours. Following filtration, the filtrate is concentrated, dissolved in methylene chloride, passed through magnesol and recrystallized from methylene chloride/hexane to afford ethyl $\alpha$-cyano-$\alpha$($\alpha,\alpha,\alpha$-trifluoro-p-tolyl)-4-morpholinebutyrate as cream colored crystals, m.p. 96°–97° C.

A solution of 38.0 g. of the preceding compound, 9.0 g. of hydrazine hydrate and 600 ml. of ethanol is refluxed for 24 hours. The solution is treated with activated charcoal, filtered and the filtrate concentrated. The residue is crystallized from methylene chloride/hexane to give 6-($\alpha,\alpha,\alpha$-trifluoro-p-tolyl)-4,5-dihydro-3(2H)-pyridazinone as cream colored crystals, m.p. 177°–178° C.

A solution of 14.5 g. of the preceding compound and 10.4 g. of bromine in 150 ml. of acetic acid is heated slowly on a steam bath until complete discoloration occurs. Heating is continued for an additional 30 minutes followed by pouring onto crushed ice. The resulting solid is filtered, washed with water to give 6-($\alpha,\alpha,\alpha$-trifluoro-p-tolyl)-3(2H)-pyridazinone as off-white crystals, m.p. 191°–193° C.

A mixture of 11.0 g. of the preceding compound and 150 ml. of phosphorus oxychloride is heated on a steam bath for 5 hours. The solution is concentrated free of solvent and the residue is washed with cold water to yield 3-chloro-6-($\alpha,\alpha,\alpha$-trifluoro-p-tolyl)pyridazine as a white solid, m.p. 186°–188° C.

A mixture of 4.50 g. of 3-chloro-6-($\alpha,\alpha,\alpha$-trifluoro-p-tolyl)pyridazine, 2.09 g. of formylhydrazine and 100 ml. of n-butanol is stirred and refluxed for 3 days. The solvent is removed and the residue dissolved in methylene chloride, passed through magnesol and the solid from the filtrate recrystallized from methylene chloride/hexane to afford the product as white crystals, m.p. 160°–161° C.

EXAMPLE 30

Preparation of 3-methyl-6-($\alpha,\alpha,\alpha$-trifluoro-p-tolyl)-1,2,4-triazolo[4,3-b]pyridazine A mixture of 4.50 g. of 3-chloro-6-($\alpha,\alpha,\alpha$-trifluoro-p-tolyl)pyridazine, 2.58 g. of acethydrazide and 100 ml. of n-butanol is heated at reflux temperature for 3 days. The solvent is removed and the residue dissolved in methylene chloride, passed through magnesol and the solid from the filtrate recrystallized from methylene chloride/hexane to afford the product as tan crystals, m.p. 199°–201° C.

EXAMPLE 31

Preparation of 6-(m-chlorophenyl)-1,2,4-triazolo[4,3-b]pyridazine

The procedure of Example 15 is repeated substituting an equimolecular amount of 3-chloro-6-(m-chlorophenyl)pyridazine for the 3-chloro-6-(p-chlorophenyl)pyridazine employed in that example. There is thus obtained the title compound in equally good yield; m.p. 175°–177° C.

EXAMPLE 32

Preparation of 3-methyl-6-(m-chlorophenyl)-1,2,4-triazolo[4,3-b]pyridazine

Following the general procedure of Example 12, 6-(m-chlorophenyl)-4,5-dihydro-3(2H)-pyridazinone is converted to 6-(m-chlorophenyl)-3-hydrazinopyridazine which is treated with acetyl chloride to give the title compound, m.p. 165°–167° C.

EXAMPLE 33

Preparation of 3,8-dimethyl-6-(m-tert-butylphenyl)-1,2,4-triazolo[4,3-b]pyridazine The general procedure of Example 28 is repeated but replacing the 3-chloro-4-methyl-(p-chlorophenyl)pyridazine employed in that example with 3-chloro-4-methyl-(m-tert-butylphenyl)pyridazine whereby the title compound is obtained in equally good yield.

We claim:

1. The method of meliorating anxiety in a mammal which comprises administering internally to said mammal an effective amount of a compound selected from the group consisting of those of the formula:

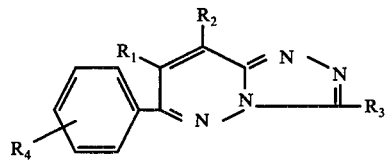

wherein $R_1$, $R_2$, and $R_3$ are each individually selected from the group consisting of hydrogen and alkyl having up to 3 carbon atoms and $R_4$ is meta or para fluoro, chloro, bromo, cyano, trifluoromethyl, nitro or amino with the proviso that at least one of $R_1$ and $R_2$ is hydrogen; and the pharmacologically acceptable acid-addition salts thereof.

2. The method according to claim 1 wherein $R_1$ is hydrogen, $R_2$ is hydrogen, $R_3$ is methyl, and $R_4$ is 3-chloro.

3. The method according to claim 1 wherein $R_1$ is methyl, $R_2$ and $R_3$ are hydrogen, and $R_4$ is 3-cyano.

4. The method according to claim 1 wherein $R_1$, $R_2$ and $R_3$ are hydrogen and $R_4$ is 4-fluoro.

5. The method according to claim 1 wherein $R_1$ is hydrogen, $R_2$ is hydrogen, $R_3$ is methyl and $R_4$ is 4-trifluoromethyl.

6. The method according to claim 1 wherein $R_1$ is hydrogen, $R_2$ is hydrogen, $R_3$ is hydrogen and $R_4$ is 3-chloro.

7. The method according to claim 1 wherein $R_1$ and $R_2$ are hydrogen, $R_3$ is methyl, and $R_4$ is 3-trifluoromethyl.

8. The method according to claim 1 wherein $R_1$ and $R_2$ are hydrogen, $R_3$ is methyl, and $R_4$ is 4-fluoro.

9. The method according to claim 1 wherein $R_1$, $R_2$ and $R_3$ are hydrogen and $R_4$ is 3-trifluoromethyl.

10. A therapeutic composition in dosage unit form useful for meliorating anxiety in mammals comprising from about 0.3 milligram to about 10.0 milligrams per kilogram of body weight per daily dosage unit, in association with a pharmaceutical carrier, of a compound selected from the group consisting of those of the formula:

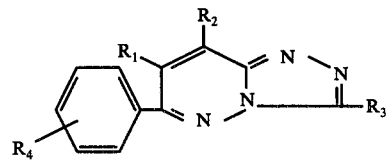

wherein $R_1$, $R_2$, and $R_3$ are each individually selected from the group consisting of hydrogen and alkyl having up to 3 carbon atoms and $R_4$ is meta or para fluoro, chloro, bromo, cyano, trifluoromethyl, nitro or amino with the proviso that at least one of $R_1$ and $R_2$ is hydrogen; and the pharmacologically acceptable acid-addition salts thereof.

* * * * *